(12) United States Patent
Malm et al.

(10) Patent No.: US 10,213,170 B2
(45) Date of Patent: Feb. 26, 2019

(54) POSITIONING OF PARTIAL VOLUMES OF AN ANATOMY

(71) Applicant: PLANMED OY, Helsinki (FI)

(72) Inventors: Juhamatti Malm, Helsinki (FI); Tapio Laukkanen, Espoo (FI)

(73) Assignee: PLANMED OY, Helsinki (FI)

( * ) Notice: Subject to any disclaimer, the term of this patent is extended or adjusted under 35 U.S.C. 154(b) by 272 days.

(21) Appl. No.: 15/037,787

(22) PCT Filed: Dec. 1, 2014

(86) PCT No.: PCT/FI2014/050938
§ 371 (c)(1),
(2) Date: May 19, 2016

(87) PCT Pub. No.: WO2015/079121
PCT Pub. Date: Jun. 4, 2015

(65) Prior Publication Data
US 2016/0296180 A1    Oct. 13, 2016

(30) Foreign Application Priority Data

Nov. 29, 2013 (FI) ...................................... 20130362

(51) Int. Cl.
*A61B 6/04* (2006.01)
*G01N 23/04* (2018.01)
(Continued)

(52) U.S. Cl.
CPC .............. *A61B 6/0492* (2013.01); *A61B 6/03* (2013.01); *A61B 6/032* (2013.01); *A61B 6/08* (2013.01); *A61B 6/4275* (2013.01); *A61B 6/4417* (2013.01); *A61B 6/4435* (2013.01); *A61B 6/4441* (2013.01); *A61B 6/461* (2013.01); *A61B 6/50* (2013.01); *A61B 90/361* (2016.02); *G01N 23/04* (2013.01); *A61B 6/488* (2013.01); *A61B 2090/373* (2016.02); *G01N 2223/309* (2013.01)

(58) Field of Classification Search
CPC .... A61B 6/00; A61B 6/03; A61B 6/04; A61B 6/0492; A61B 6/4435; A61B 6/4417; A61B 6/461; A61B 90/00; A61B 90/361; A61N 5/1048; A61N 5/1049; A61N 2005/1059
USPC .................................. 378/4, 20, 62, 63, 205
See application file for complete search history.

(56) References Cited

U.S. PATENT DOCUMENTS

2002/0023652 A1   2/2002   Riaziat et al.
2003/0133602 A1   7/2003   Bani-Hashemi
(Continued)

FOREIGN PATENT DOCUMENTS

EP     1484016 B1     7/2013
WO    2011135186 A1   11/2011

*Primary Examiner* — Jurie Yun
(74) *Attorney, Agent, or Firm* — Fay Sharpe LLP

(57) ABSTRACT

The invention relates to positioning of partial volumes of an anatomy in connection with an imaging process. According to the invention, a photograph is taken of an object arranged in an imaging station by a camera arranged in connection with the imaging station, which image of the anatomy is presented on a display but as transferred into a new position with respect to the imaging station. When this image and a substantially real time image taken of the imaging station are presented on a display one upon another, it is possible to follow on the display how the object being imaged positions in relation to said image taken of the anatomy transferred into the new position.

7 Claims, 4 Drawing Sheets

(51) Int. Cl.
*A61B 6/03* (2006.01)
*A61B 6/08* (2006.01)
*A61B 6/00* (2006.01)
*A61B 90/00* (2016.01)

(56) References Cited

U.S. PATENT DOCUMENTS

2003/0225325 A1 12/2003 Kagermeier et al.
2006/0269046 A1 11/2006 Schmitt
2010/0290707 A1 11/2010 Wang et al.
2012/0238871 A1 9/2012 Pfister
2012/0257714 A1 10/2012 Graumann et al.
2013/0121468 A1 5/2013 Ohta et al.

POSITIONING OF PARTIAL VOLUMES OF AN ANATOMY

FIELD OF INVENTION

The invention relates to mutual positioning of partial volumes of an anatomy in connection with an imaging process.

BACKGROUND OF INVENTION

Conventional apparatuses employed in medical x-ray imaging which are most simple as for their basic structure comprise a source of radiation which is used together with a film cassette separate from the source of radiation. Hospitals commonly also use so-called C-arch x-ray apparatuses in which the source of radiation and the receiver of image information are arranged at the opposite ends of the arch-shaped arm part. Conventionally, a group of apparatus completely of its own consists of large-size and extremely expensive computed tomography apparatus, into which a patient is typically positioned for imaging in a lying position inside a ring-shaped or tubular structure.

As conventional computed tomography apparatus have been quite massive and expensive, acquiring them e.g. for the use of hospital emergency rooms has not been possible in practice. On the other hand, it has also been typical for commercial computed tomography apparatus that they are not necessarily designed for imaging some specific anatomy or anatomies but they are more or less general imaging apparatus. If one wishes to image e.g. the patient's whole torso, the imaging station arranged to the apparatus as well as other dimensions of the apparatus must have been implemented in respective proportions.

More lightweight computed tomography apparatus versions have been developed as well. As an example of prior art solutions, a reference can be made to a structure disclosed e.g. in the WO publication 2011/135186. In such apparatus, imaging means arranged to move around an imaging station are arranged within a ring-shaped O-arm, supported from its side.

In the more lightweight apparatus according to the prior art as referred to above cone beam tomography KIM may be used. There, one criterion which limits the size of a volume getting imaged (FOV—Field of View) is the dimensions of the imaging detector, which for obvious reasons cannot be arranged in such context to be very large. When considering imaging an extremity, for example, it is clear that when using such an imaging apparatus it is possible to image only a single partial volume of the extremity by one mutual positioning of the patient and the imaging apparatus. Then it becomes necessary to position the anatomy in the imaging apparatus anew, for imaging the next partial volume, and realizing the re-positioning in relation to the previous positioning in an exactly desired way can be a challenge.

BRIEF DESCRIPTION OF INVENTION

The object of the present invention is to advance the state of the art concerning e.g. the less expensive and smaller x-ray imaging apparatus like those referred to above. A special object of the invention is to advance development particularly regarding x-ray imaging apparatus of the above-described type comprising a ring-shaped arm part and being of relatively small size. The construction, characteristics and dimensions of such apparatus remarkably differ in many respects from the conventional hospital computed tomography apparatus and in these apparatus the patient is positioned for imaging in a way other than in conventional computed tomography apparatus, in which the patient is set to lay down on an imaging platform.

Especially an object of the invention is an arrangement which eases positioning of a patient in situations in which one needs to image an anatomy at more than one location so as to get the entire desired volume imaged.

Essential features of the invention are described in the accompanying claims. Especially essential for the invention is to arrange a means to the imaging apparatus to take photographs or video images of the imaging area of the apparatus and, on the other hand, a means to present such camera image on a display in a specific way.

The invention facilitates positioning of a patient and can make it unnecessary to use e.g. scout x-ray images, which are taken by using a small radiation dose, for positioning purposes. The invention can also be arranged to speed up processing of image information to combine the partial volumes imaged after the imaging, as there is at least moderately accurate information available regarding how the sets of coordinates of the partial volumes imaged have located in relation to each other.

Next, the invention and its preferable embodiments will be described in more detail and also with reference to the enclosed figures.

DETAILED DESCRIPTION OF INVENTION

The process demonstrated by FIGS. 1-4 can be thought of as a method for positioning an anatomy for imaging, in which method a first partial volume is imaged first and a second partial volume after that. These partial volumes are imaged such that the mutual positioning of the anatomy and the imaging means is changed between the imagings. This change in the positioning can be implemented such that the first and the second partial volumes will partially cover a same volume of the anatomy being imaged, but the invention can also enable a controlled positioning of partial volumes such that the partial volumes do not intersect each other.

Figure 1:
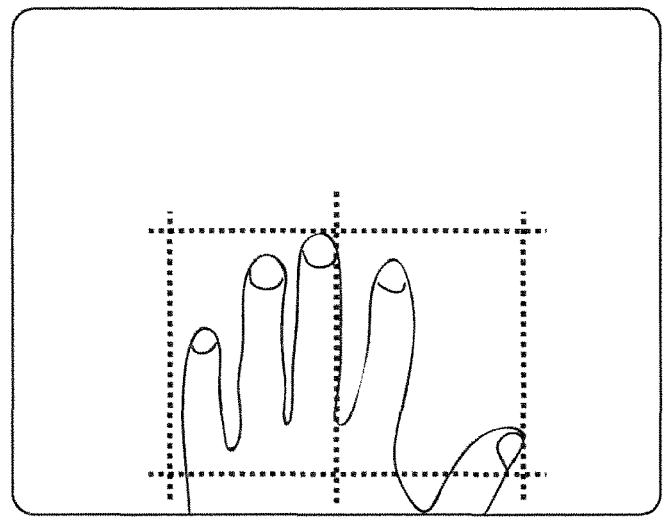
FIG. 1 shows photographing a first partial volume of an object positioned in an imaging area of an imaging apparatus.
Figure 2:
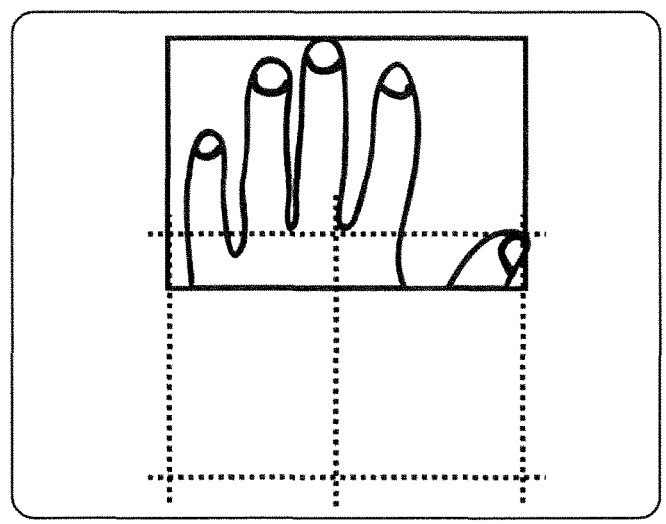
FIG. 2 shows an image in which the image shown in FIG. 1, taken when the object is located at an imaging position for the first partial volume, is projected as placed in a new desired location considering imaging the next partial volume.

During imaging of the first partial volume (FIG. 1), a photograph or a still video image is taken of the anatomy positioned at the imaging station by a camera arranged in connection with the imaging station, which image is presented on the display as moved to a new position in relation to the imaging station (FIG. 2). Then, this image and a real time image of the imaging station are presented an the display one upon another, and positioning of the anatomy being imaged (FIG. 3) to meet the image of the first partial volume presented on the display as moved into the new position is observed from the display (FIG. 4).

FIGS. 1-4 are not intended to show any particular embodiment of the invention but only to demonstrate the invention. Thus, e.g. the outermost rectangles of FIGS. 1-4 plotted by a continuous line can be thought of as demonstrating a display screen, the area of the imaging area or of the imaging station seen by the camera, or the field of view (FOV) from which a tomographic image can be reconstructed using x-ray image information the imaging apparatus generates.

Figure 3:
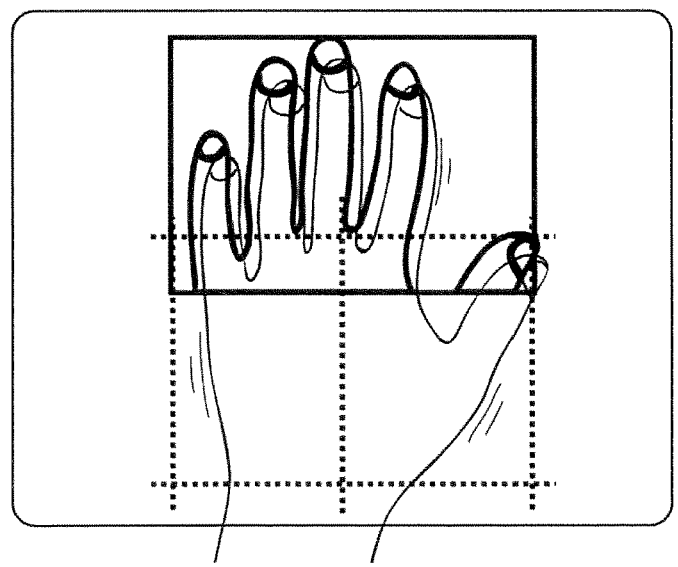
FIG. 3 demonstrates an image being presented on a display in which the object being imaged is being positioned at a new location for imaging the next partial volume.
Figure 4:
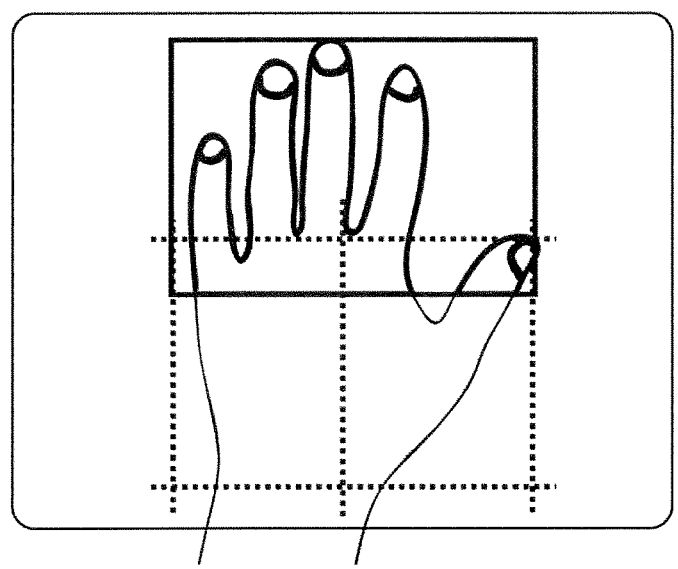
FIG. 4 demonstrates a situation in which the object has been managed to be positioned at the new location for imaging the next partial volume.

The smaller rectangular areas of FIGS. 1-4 can in turn be thought of as relating to the image transfer process according to the invention such that the dashed line area of FIG. 1 represents an area (anatomy) of the image taken by the camera from the imaging station selected to be transferred, and FIG. 2 shows how the image taken of the area (anatomy) selected in FIG. 1 has been transferred (the area defined by the continuous line). FIG. 2 has been used as a base for FIGS. 3 and 4 and hence they also include the area of FIG. 1 plotted by the dashed line. Concerning the steps shown in FIGS. 3 and 4, the area of FIG. 1 plotted by the dashed line has no particular function but to demonstrate the process, also that area is carried over to FIGS. 3 and 4. Essential to FIGS. 3 and 4 is presenting the image taken during the phase shown in FIG. 1, that is the image located at a transferred position according to FIG. 2 (the image shown within the area defined by the continuous line), on a display in a camera picture taken from the imaging area.

When it was noted above that the dashed line area of FIG. 1 can be considered presenting an area of the image taken by the camera selected to be transferred, it is also possible to consider that the camera has been arranged to photograph only the dashed line area, which picture as such will then be arranged to be shown on the display at a new position. If only this dashed line area is photographed and if only it is presented on the display during the steps which FIGS. 3 and 4 present, the area of the anatomy whose positioning to a desired location can then be followed is correspondingly smaller.

Within limits the camera arrangement of an apparatus and the dimensions of its imaging area allow for, a controlled repositioning of the anatomy can also be made concerning partial volumes which do not intersect. Considering e.g. a situation in which there are two points of interest in an extremity, located at distance from each other and including a partial volume in-between regarding which there is no need to acquire actual x-ray image information. As one knows when proceeding as described above how the photograph taken during the step according to FIG. 1 has been transferred to the location according to FIG. 2, one also knows where the partial volume imaged according to step 4 locates in relation to the first partial volume imaged in the step according to FIG. 1.

Figure 5:
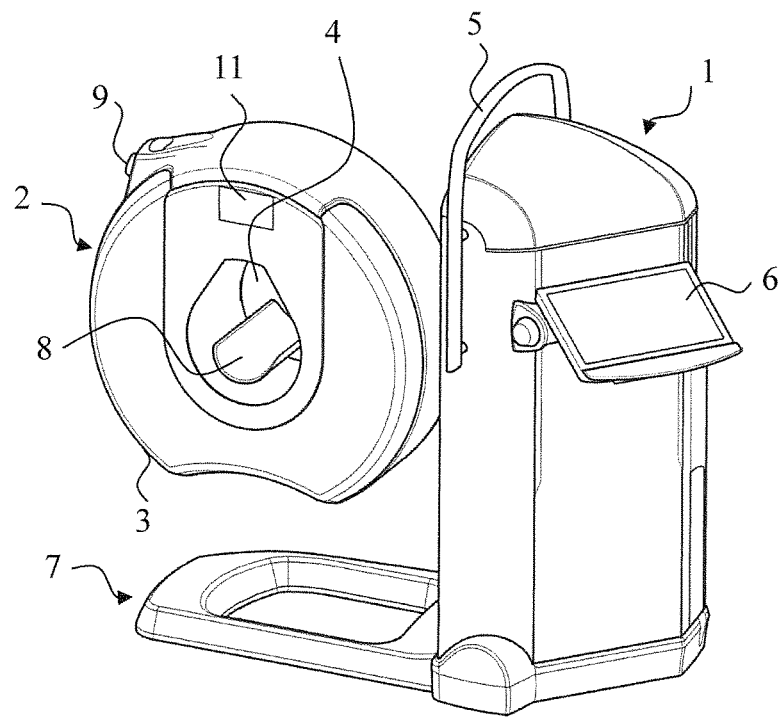
FIGS. 5 and 6 show solutions for apparatus applicable for use in the invention.

The basic idea of the invention is preferable to be applied for example in an imaging apparatus according to FIG. 5. The basic structure of the apparatus includes a support construction (1) which supports a substantially ring-shaped structure (2), inside which the x-ray imaging means (21, 22) of the apparatus are positioned and which in this context is also referred to as an O-arm. To this O-arm (2) is arranged an examination opening (4) into which the anatomy to be imaged is positioned. FIG. 1 further shows a patient support handlebar (5) arranged to the support construction (1), a user interface (6) being in functional connection with a control system of the apparatus, a possibly detachably attached pedestal or base part (7) projecting substantially in the direction of the O-arm, and a positioning support (8) arranged in the examination opening (4). According to the embodiment of the invention shown in FIG. 1, the display (11) belonging to the apparatus is arranged substantially on the surface of the ring-shaped structure (2), at its upper edge.

Mounting of the structure (2) supporting the imaging means to the support construction (1) can be arranged to enable adjustment of the height position of the O-arm (2). Furthermore, this O-arm (2) can be arranged to be turnable in at least one direction for at least 90 degrees from the vertical position, shown in FIG. 1), to a horizontal position. The control of these manoeuvres can be arranged implementable, aside from the user interface (6) being connected with the control system of the apparatus also by means of a joy stick (9) arranged in connection with the O-arm (2) and/or the support frame (1).

Figure 6:
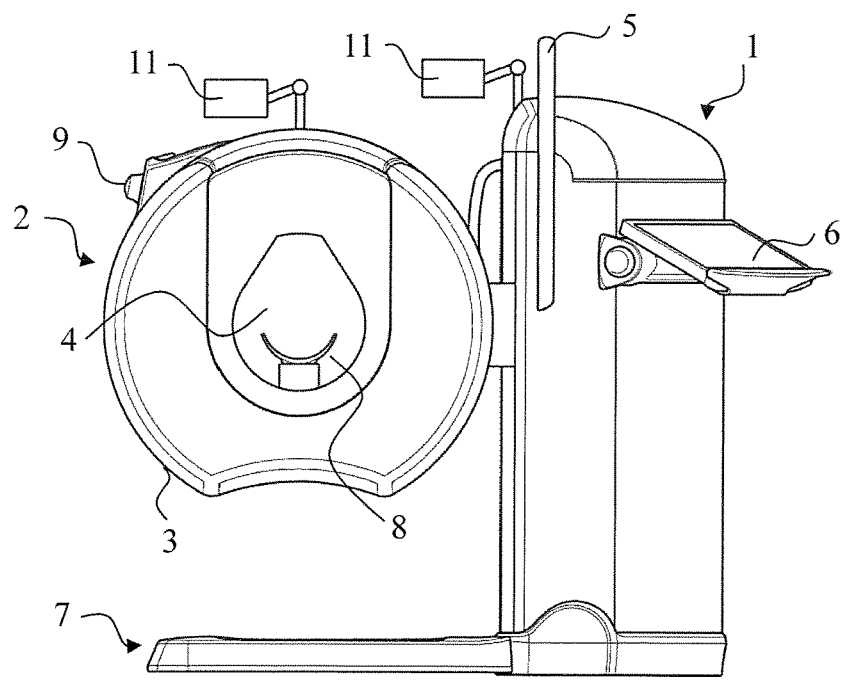

FIG. 6 shows two alternative ways to position the display (11) in connection with the apparatus. The display is preferably positioned to the apparatus at a location which is visible to the patient when e.g. a patient's leg is being imaged. The display (11) can be arranged to the ring-shaped structure (2) both as fixed and as movably attached. The connection can be arranged to enable either adjusting orientation of the display (11) with respect to the ring-shaped structure (2), adjusting clearance and/or location of the display (11) with respect to the ring-shaped structure (2), or it can be arranged with some or all of these degrees of freedom of movement. Alternatively, the display (11) can be attached to the supporting structure (1), or a separate display (11) can be set to the supporting structure (1) which display (11) can be arranged with the degrees of freedom of movement as described above but with respect to the supporting structure (1).

Figure 7:
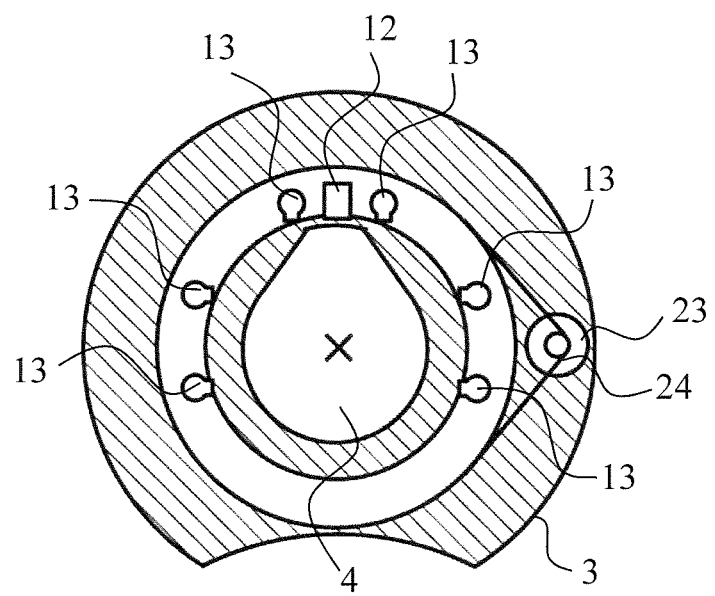
FIG. 7 shows, as simplified, how the structure according to FIGS. 5 and 6 can be arranged with a camera aligned at the imaging area of the apparatus.

In the embodiment presented in FIG. 7, a video camera (12) aligned inside the examination opening (4) is arranged in connection with the ring-shaped structure (2) of the. In principle, the camera (12) can be arranged to the ring-shaped structure (2) outside its cover, particularly at the opposite side of the examination opening from which the extremity to be imaged is designed to be brought into the examination opening, but in a preferable embodiment of the invention the video camera (12) is arranged inside the ring-shaped structure (2) and at least a part of an inner surface of the said ring-shaped structure (2) is arranged transparent or to comprise an opening through which the camera (12) is aligned at the examination opening (4), like substantially at a positioning support (8) arranged in the examination opening.

However, it is essential that the apparatus has at least one photography or video camera (12) which is arranged to image an imaging area of the apparatus and the control system of the apparatus presents on a display (11) one upon another a first image taken of an object positioned for tomographic imaging and an essentially real time image taken of the imaging area such that the object visible in the first image positioned for tomography imaging is moved to a position in the imaging area different from where it was in when the first image was taken. The camera can be arranged inside the ring-shaped structure (2) and at least part of an inner surface of the ring-shaped structure (2) is arranged transparent or to contain an opening through which the camera (12) is aligned or can be aligned at the examination opening (4). If there is a positioning support (8) arranged in the examination opening (4) for positioning an anatomy to be imaged for x-ray imaging, the camera (12) is preferably aligned or arranged to be aligned substantially at the positioning support (8).

It is obvious for one skilled in the art that as for its details, the present invention may be implemented also in other ways than according to the embodiments of the invention described above.

The invention claimed is:

1. A method for positioning an anatomy for x-ray imaging said method comprising x-ray imaging a first partial volume of the anatomy, wherein in connection with x-ray imaging of the first partial volume, a photograph or a still video image of the anatomy positioned in an imaging station is taken by a camera arranged in connection with the imaging station, wherein said photograph or still video image of said anatomy is presented on a display as a positioning image in which said anatomy is shown at a new position in relation to the imaging station at the time of taking said photograph or still video image and wherein the positioning image and a real time image of the imaging station are then presented on said display one upon another such that the anatomy being x-ray imaged is positioned to meet the new position of the anatomy according to the positioning image using observation of the display such that x-ray imaging of a second partial volume of the anatomy different from the first partial volume is performed.

2. The method according to claim 1, wherein between the x-ray imaging of the first partial volume and the second partial volume of the anatomy, mutual positioning of the anatomy and imaging means is changed such that the second partial volume of the anatomy being imaged covers in part the first partial volume of the anatomy being imaged.

3. The method of claim 1 wherein positioning of the anatomy being imaged to meet the new position is achieved by adjustment of a ring shaped structure housing a source of radiation or a support for the anatomy.

4. The method of claim 3 wherein said adjustment is controlled by a joy stick.

5. Medical computed tomography (CT) imaging apparatus, which apparatus comprises:
   a support construction, which is arranged to support a substantially ring-shaped structure supporting imaging means, which imaging means includes a source of radiation configured to generate a radiation beam and a receiver of image information, which imaging means is arranged inside said substantially ring-shaped structure supporting the imaging means on substantially opposite sides, and configured to be moved inside said ring-shaped structure supporting the imaging means,
   a control system for controlling at least selective functions of the apparatus,
   which apparatus includes in said ring-shaped structure supporting the imaging means an examination opening, in which an anatomy to be imaged is positionable for imaging,
   which apparatus is arranged with at least one photography or video camera and at least one display arranged in functional connection with said at least one photography or video camera, said at least one photography or video camera being arranged in connection with said substantially ring-shaped structure and as aligned or suitable for alignment to take a photograph or a still video image of the anatomy positioned for CT imaging in said examination opening within an imaging area of the apparatus, the control system of the apparatus being configured to present on said at least one display one upon another on top of each other a first image and a second image, wherein the first image is said photograph or still video image of the anatomy positioned for CT imaging but in which said anatomy is shown in a new position in relation to the imaging area at the time of taking said photograph or still video image, and the second image is another, at least essentially real time photograph or still video image of the imaging area taken by said at least one photography or video camera.

6. The imaging apparatus according to claim 5, wherein said at least one camera is arranged inside said substantially ring-shaped structure and at least a portion of an inner surface of said substantially ring-shaped structure has been arranged transparent or to comprise an opening through which said at least one camera is aligned or can be aligned at said examination opening.

7. The imaging apparatus according to claim 5, wherein a positioning support is arranged in said examination opening for positioning the anatomy to be imaged for CT imaging and said at least one camera is aligned or arranged to be aligned substantially at said positioning support.

* * * * *